(12) United States Patent
Kaemper et al.

(10) Patent No.: US 8,701,656 B2
(45) Date of Patent: Apr. 22, 2014

(54) INHALER

(75) Inventors: Markus Kaemper, Breckerfeld (DE);
Jens Besseler, Bingen am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 434 days.

(21) Appl. No.: 12/990,550

(22) PCT Filed: Apr. 22, 2009

(86) PCT No.: PCT/EP2009/002912
§ 371 (c)(1),
(2), (4) Date: Nov. 30, 2010

(87) PCT Pub. No.: WO2009/132791
PCT Pub. Date: Nov. 5, 2009

(65) Prior Publication Data
US 2011/0126827 A1    Jun. 2, 2011

(30) Foreign Application Priority Data
May 2, 2008    (EP) ..................... 08008332

(51) Int. Cl.
*A61M 16/00*    (2006.01)
*A61M 15/00*    (2006.01)

(52) U.S. Cl.
USPC ............. 128/202.22; 128/203.15; 128/203.21

(58) Field of Classification Search
USPC .............. 128/203.15, 203.19, 203.21, 202.22
See application file for complete search history.

(56) References Cited

U.S. PATENT DOCUMENTS

| 2002/0026938 A1 | 3/2002 | Hodson et al. |
| 2007/0181123 A1 | 8/2007 | Houzego |
| 2008/0289627 A1 * | 11/2008 | Rohrschneider et al. ........................ 128/200.23 |

FOREIGN PATENT DOCUMENTS

| EP | 1774984 A1 | 4/2007 |
| WO | WO 2008058964 A2 * | 5/2008 |

OTHER PUBLICATIONS

International Search Report, Form PCT/ISA/210, for corresponding PCT/EP2009/002912; date of mailing: Oct. 20, 2009.

* cited by examiner

*Primary Examiner* — Oren Ginsberg
*Assistant Examiner* — Jennifer M Deichl
(74) *Attorney, Agent, or Firm* — Michael P. Morris; Mary-Ellen M. Devlin

(57) ABSTRACT

An inhaler (1) is proposed for delivering a preferably powdered formulation from a blister strip (3) having a plurality of blister pockets (4). The inhaler comprises a life span blocking device (31) which blocks opening of a cover (15) of the inhaler in a blocking state by means of locking element (39) interlocking the cover with a housing (19) of the inhaler.

13 Claims, 9 Drawing Sheets

INHALER

The present invention relates to an inhaler for discharging a preferably powdered formulation in multiple doses one after the other, i. e. to a multi-dose inhaler.

The present invention relates to the delivery and atomization of a formulation particularly for inhalation or for other medical or therapeutic purposes. Particularly preferably the present invention relates to the delivery of medical, pharmaceutical and/or therapeutic formulations which in particular contain or consist of at least one active substance. During atomization (discharging) an aerosol or a spray cloud is produced having, particularly for inhalation, very fine, solid and/or liquid particles, preferably in the range from 1 to 10 μm.

The formulation is preferably a powder. Particularly preferably, the invention therefore relates to a powder inhaler. The term "formulation" according to the invention preferably also includes liquids, however, while the term "liquid" is to be understood in the broad sense as including inter alia solutions, suspension, solutions (mixture of solution and suspension), dispersions, mixtures thereof or the like.

The present invention relates to an inhaler or other atomizer for discharging a preferably powdered formulation from a reservoir or carrier such as a blister strip or other preferably disc-shaped or band-shaped carrier, having a plurality of receptacles or blister pockets containing the formulation in doses. The term "inhaler" is therefore preferably to be understood generally as including other atomizers or dispensers for delivering a preferably pre-metered formulation.

WO 2007/134792 A1 discloses an inhaler for delivering a powered formulation from a blister strip with a plurality of blister pockets. There is a need to prevent re-use of the inhaler or its carrier formed by the blister strip when the inhaler has been emptied.

Object of the present invention is to provide an improved inhaler wherein further use or operation of the inhaler can be blocked, inparticular in a very secure and/or simple manner, when operation or use of the inhaler reaches or exceeds a predetermined number of operations or uses.

The above object is achieved by an inhaler according to claim 1 or 6. Advantageous embodiments are subject of the subclaims.

According to the present invention, a life span blocking device (LSB) is provided for blocking further use or operation of the inhaler in a blocking state, in particular when operation or use of the inhaler reaches or exceeds a predetermined number of operations of uses. The "blocking state" shall preferably also encompass a situation when the LSB is activated, but blocking of any further operation or use of the inhaler is actually blocked by the LSB after termination of the current or next operation or use of the inhaler.

According to a first aspect of the present invention, the LSB blocks movement or opening of a cover associated to an outlet or mouthpiece of the inhaler. This allows simple construction and/or secure blocking and/or facilitates intuitive understanding of the blocking for a user.

According to an independent second aspect of the present invention, the LSB comprises a locking element which is biased into an interlocking position for blocking further use or operation of the inhaler, wherein the locking element is held in a non-interlocking position and released or forced into interlocking position when the blocking state is entered. This allows simple construction and/or secure blocking.

Further aspects, features, properties and advantages of the present invention will become apparent from the claims and following description of preferred embodiments with reference to the drawings. In the drawings:

In the figures, the same reference numerals have been used for identical or similar parts and components; in particular, similar or corresponding advantages and/or properties are obtained even if the associated description is not repeated.

Figure 1:
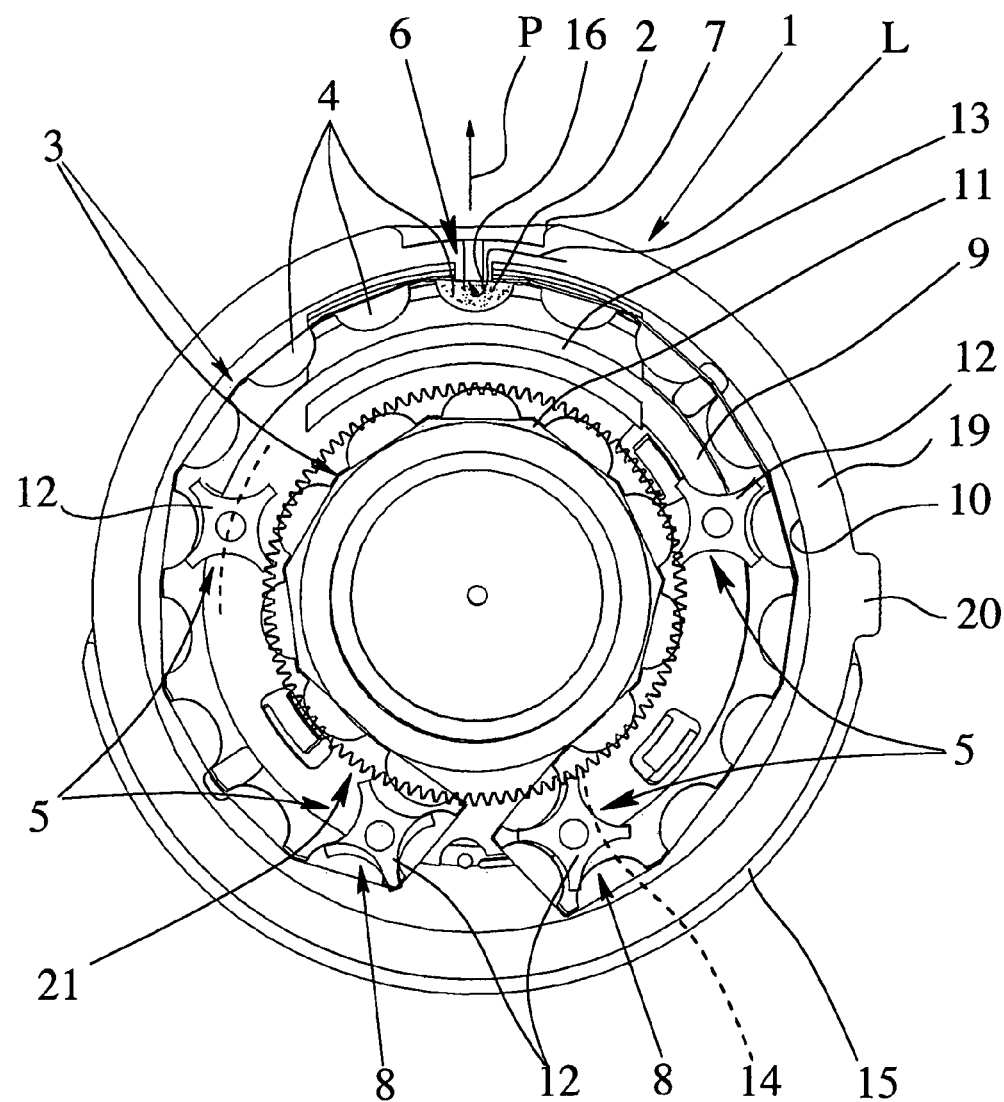
FIG. 1 is a schematic view of an inhaler according to a first embodiment in the open state.
Figure 2:
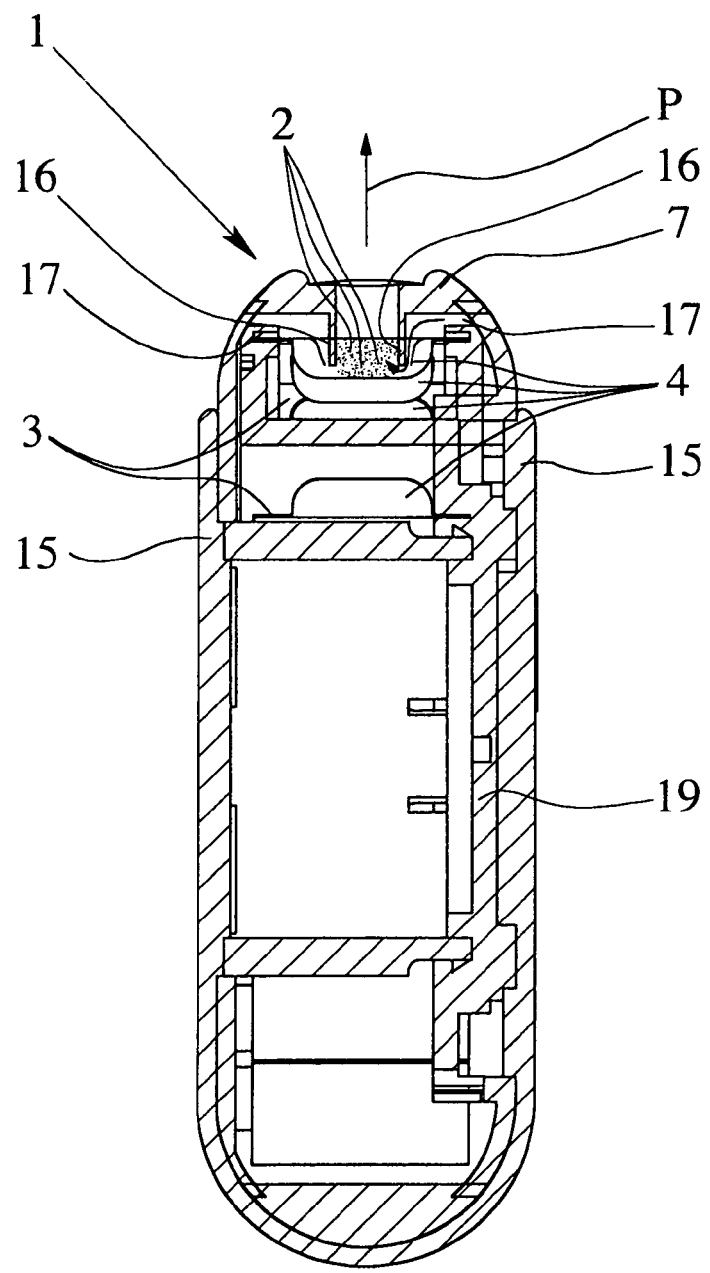
FIG. 2 is a section through a part of the inhaler in the region of a mouthpiece.

FIG. 1 shows in a highly schematic representation an inhaler 1 according to a first embodiment, in a cut-away or open state without a lid. FIG. 2 shows the inhaler 1 in a schematic section. The first embodiment serves preferably general explanation purposes, but shall comprise a life span blocking device as described later with reference to the second and third embodiments.

The inhaler 1 is preferably portable in construction. Particularly preferably, it operates purely mechanically.

The inhaler 1 serves to deliver a preferably powdered formulation 2 in the sense described hereinbefore from a preferably band- or strip-shaped carrier, particularly a blister strip 3, having a plurality of receptacles, especially blister pockets 4 containing the, in particular, loose formulation 2 in doses, i.e. in pre-metered form. The carrier forms in particular a closed loop, i.e. it is of circular or endless construction. Alternatively, the carrier may be wound or stored in any other suitable manner. For inhalation and particularly during inhalation, preferably one dose of the formulation 2 is taken from a receptacle or blister pocket 4.

However, the inhaler 1 could also be adapted for other carriers.

Preferably, the inhaler 1 is a dry powder inhaler.

The inhaler 1 comprises preferably has a conveying device 5 for advancing or conveying the carrier stepwise, preferably by means of at least one (blister driving) wheel 12.

The inhaler 1 comprises preferably a removing device 6 (in particular a piercer) for individually opening the receptacles and/or removing the doses of formulation 2. In particular the removal device 6 is constructed so that the receptacles can be opened (e.g. pierced) individually and successively from the outside. This will be explained later in more detail. The removal device 6 preferably also connects the opened receptacle fluidically to an outlet or mouthpiece 7 or any other end piece of the inhaler 1.

When inhaling or during delivering, an air current L of ambient air can be sucked in and/or flows through the opened receptacle in order to deliver the respective dose with the ambient air through the associated mouthpiece 7 of the inhaler 1, as indicated by the arrow P in FIG. 1. Thus, the inhaler 1 is preferably a passive inhaler.

However, the inhaler 1 could also be an active inhaler where the air stream or any other gas stream, which is not generated by breathing of a user, but e.g. by a pump, compressor, propellant, liquefied or compressed gas, or the like, discharges the formulation 2.

The mouthpiece 7 of the inhaler 1 is preferably stationary and/or of rigid construction and/or is formed on or formed by a housing 19 of the inhaler 1 and/or attached or rigidly connected to the housing 19.

Instead of the mouthpiece 7 the inhaler 1 may also have another end piece, for example for nasal or other routes of administration for delivering the formulation 2. In particular, the inhaler 1 may also be used as a nebuliser for other purposes, e.g. for the eyes. The term "inhaler" should therefore preferably be understood in a correspondingly general sense.

In the first embodiment, the conveying device 5 preferably has two deflectors 8 for the carrier. Preferably, the carrier is guided in an annular segment 9 and/or in a channel between a peripheral or outer wall 10 and an intermediate or inner wall 11 of the inhaler 1.

The term "deflecting the carrier" or "deflector" means preferably in the present invention that the carrier is deflected by at least 90° or 160°, particularly at least substantially 180° or more.

Preferably, the inhaler 1 comprises at least one wheel 12, preferably constructed so that the carrier can be conveyed or moved by preferably interlocking engagement, so that the carrier can be advanced or conveyed onwards step by step to the next receptacle by corresponding stepwise rotation of the wheel 12. This enables the formulation 2 to be removed from the individual receptacles one after another and individually taken for delivery through the removal device 6 as described later.

Preferably, the wheels 12 can be driven by a common transmission or drive means, such as a central, main or sun wheel 14, which is only partly shown in FIG. 1. In this case a kind of planet gear or transmission can be formed, in particular, with the wheels 12. The wheels 12 or optionally associated gears preferably have teeth in to allow a defined movement or conveying of the carrier. Alternatively or additionally, the wheels 12 may also be drivable, for example, by means of an encircling belt or the like as common drive means.

Thus, during the actuation of the conveying device 5 the carrier continues to be advanced or conveyed onwards, and indeed is advanced stepwise to the next receptacle for the next delivery or inhalation.

It has to be noted that any deflector 8 can be formed by a (driven) wheel 12 or loose roll or by a channel, grove, slot or the like guiding the carrier, in particular the blister strip 3, at one of its main sides and/or at least one of its longitudinal edges or the like.

Figure 3:
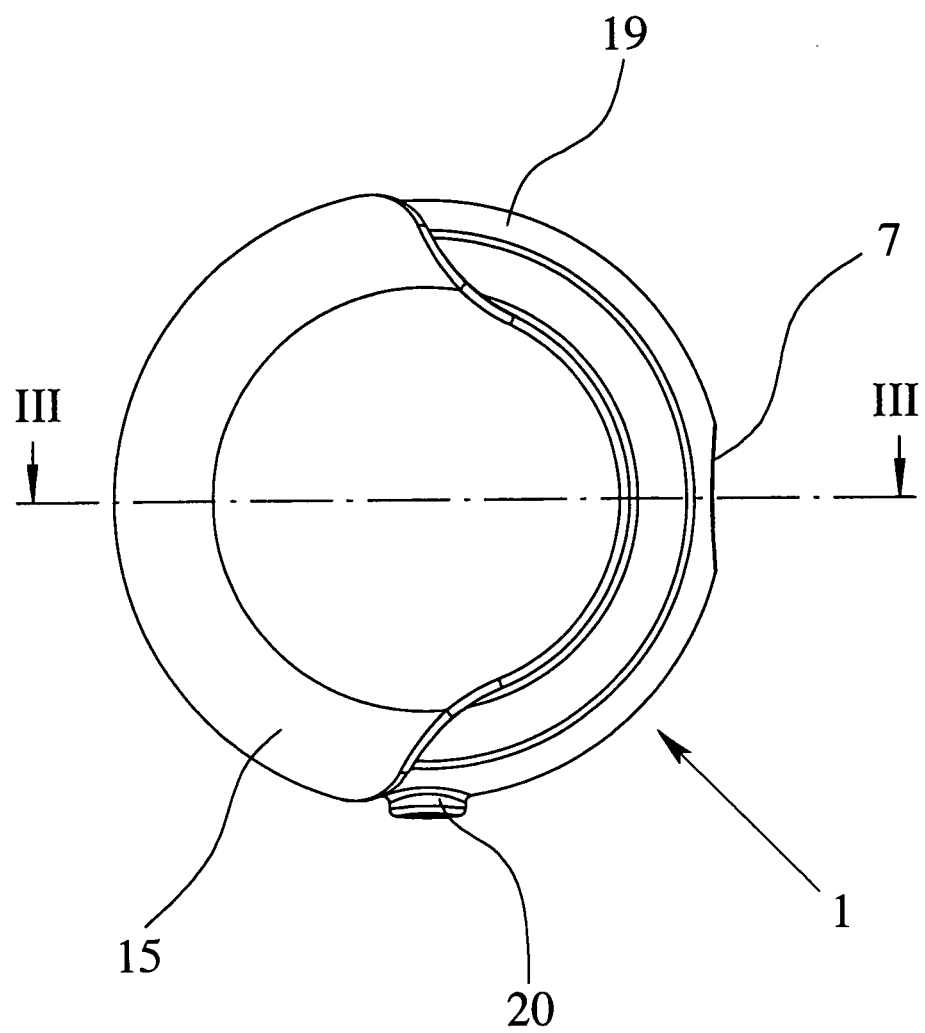
FIG. 3 is an external view of the inhaler.

The mouthpiece 7 or other end piece preferably, the inhaler 1 comprises a cover 15 associated to the outlet or mouthpiece 7 or the like. In particular, the cover 15 shown in FIG. 3 is movable, in particular pivotal, preferably in order to open and/or close the mouthpiece 7. In particular, the cover 15 is moveable between a closed position covering the outlet or mouthpiece 7, and an open position uncovering the outlet or mouthpiece 7.

FIG. 3 shows the inhaler 1 in exterior view with the cover 15 open. Preferably at least one stop, in this case a radial stop 20, is provided for limiting the pivoting movement of the cover 15.

The conveying device 5 and/or removal device 6 are preferably actuated by the opening and/or closing movement (preferably by at least part of the movement in one direction) of the cover 15. This provides a very simple and, in particular, intuitive method of actuating and using the inhaler 1. In particular, the inhaler 1 is constructed such that the carrier is advanced and a receptacle is opened and fluidically connected to the mouthpiece 7 only by means of the opening and/or closing movement of the cover 15.

The removal device 6 preferably has at least two opening elements 16 (compare FIG. 2) which are constructed in particular as piercing, tearing or cutting elements, are preferably unmovable or of fixed design, and/or are attached to the mouthpiece 7 or any other component of the inhaler 1.

The opening elements 16 on one hand and the respective receptacle or the carrier on the other hand are moveable relative to each other in order to open the respective receptacle, in particular to pierce it, and thereby establish a fluidic connection with the receptacle in question.

Preferably the relative movement is carried out by the carrier being moved by a guide element 13 (shown in FIGS. 1, 2 and 4) or in some other way or by some other means, in particular pushed transversely or perpendicularly with respect to its direction of onward movement or conveying. For this purpose the guide element 13 is correspondingly guided to be movable, particularly slideable, most preferably in the manner of a sled. This direction of movement or sliding of the carrier/guide element 13 extends in particular in the radial direction, in the embodiment shown, or in or counter to the direction of delivery or arrow P. The guide element 13 is driven or operated or shifted preferably back and forth by the opening and/or closing the cover 15. In particular, the cover 15 and the guide element 13 are coupled in a suitable manner, preferably by a transmission.

Figure 4:
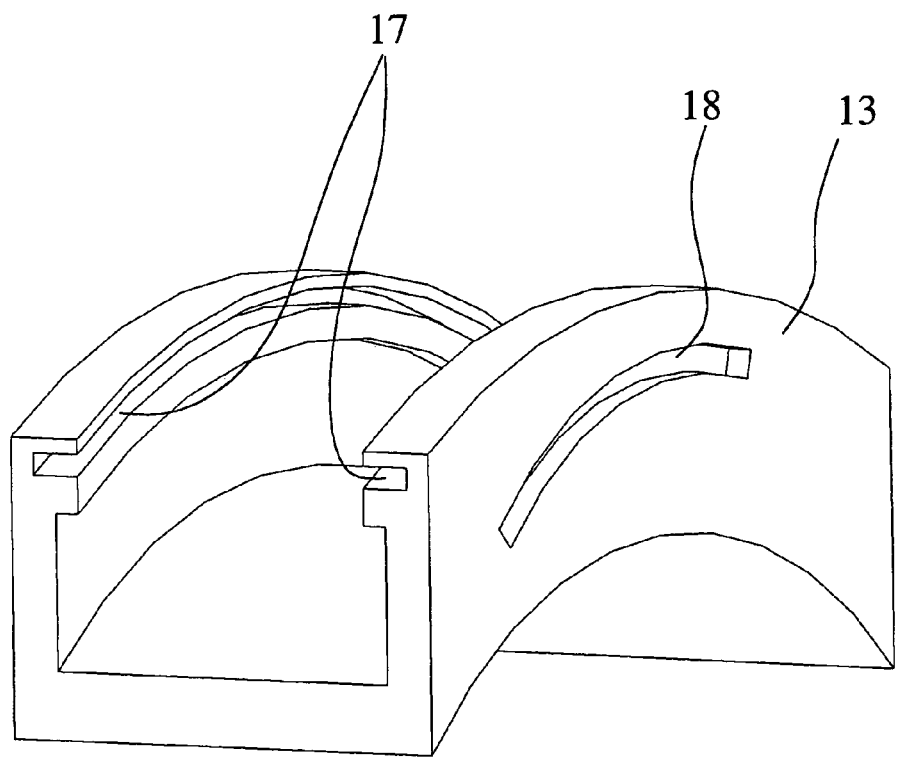
FIG. 4 is a perspective view of a guide element of the inhaler.

FIG. 4 shows in perspective view a preferred construction of the guide element 13. The guide element 13 guides the carrier preferably by interlocking engagement, e.g. the carrier engages with its longitudinal edges in opposing longitudinal grooves 17 open towards one another. However, other constructional solutions are also possible.

Moreover, FIG. 4 shows a preferably exterior sliding surface, control groove or control curve 18 on the guide element 13. The cover 15 may engage directly or indirectly in this control curve 18, so that the guide element 13 and hence the carrier are moved or displaced in the desired manner relative to the opening elements 16 for selectively opening or making contact with the respective receptacle. In particular, a sliding or forcible guidance is formed for positively moving the guide element 13 or the carrier in a defined manner as desired. However, other geared solutions or actuations are also possible. In particular, a complementary construction is possible with the control curve formed at the cover 15 and a protrusion at the guide element 13 engaging into the control curve 18.

For use, the cover 15 of the inhaler 1 is opened, for example by pivoting or rotating about a central axis of the inhaler 1. This exposes the mouthpiece 7. Before this, at the same time or subsequently, the conveying device 5 is actuated and/or the carrier is advanced to the next receptacle. This is achieved in particular by means of a suitable geared or other coupling of the cover 15 with the conveying device 5, particularly preferably with the sun wheel 14.

After the carrier has been advanced in the desired manner, and preferably as the opening or pivoting movement of the cover 15 continues, the receptacle intended for the next inhalation, and in particular already positioned relative to or underneath the opening elements 16 or removal device 6, is opened. To open it, the guide element 13 or the carrier is moved relative to the opening elements 16 such that these open the receptacle, particularly engage in a foil cover, preferably flat side or covering or lid of the next blister pocket 4 and cut it open, pierce it, tear it open, or the like. This state is illustrated in FIG. 1 and FIG. 2 in a cut away schematic section through part of the mouthpiece 7. In this state with opened blister pocket 4 fluidically connected to the mouthpiece 7, the cover 15 is fully open and the inhaler 1 is ready for delivery (discharging) or inhalation.

According to a particularly preferred alternative feature the carrier is not conveyed onward during the opening of the cover 15 but is opened only in the course of the opening movement (in particular, only at the end of the opening movement). In particular, the respective receptacle of the carrier is pierced by the opening elements 16. Particularly preferably the opening of the receptacle (blister pocket 4) is carried out by moving the carrier or the corresponding receptacle up to the preferably stationary opening elements 16.

The blister pocket 4 is fluidically connected by means of the removal device 6 and/or its opening elements 16. The open blister pocket 4 is further fluidically connected with the mouthpiece 7 or any other end piece.

Thus, the gas stream, air stream L (FIG. 1), can flow into the blister pocket 4, entrain the formulation 2 contained in the blister pocket 4 (e.g. by forming swirls in the blister pocket 4), and flow out of the blister pocket 4 through the mouthpiece 7 in order discharge the formulation 2 in nebulised form, i.e. as aerosol cloud or spray mist.

After the receptacle (blister pocket 4) has been emptied and the formulation 2 delivered, the inhaler 1 or the cover 15 can be closed again. To do this, the cover 15 is preferably rotated or pivoted counter to the direction of opening.

During the closing movement of cover 15, first of all in a first phase the opening elements 16 and the carrier are moved away from one another (in particular the carrier is moved away from the opening elements 16) so that the carrier can be moved onwards. Then in a second phase of the closing movement of the cover 15 the carrier may be moved on, so that the next receptacle is already in position or at least substantially correctly positioned. This procedure has the advantage that partial opening of the inhaler 1 or cover 15 starting from the closed position does not necessarily lead to any further movement of the carrier.

A second embodiment of the inhaler 1 is shown in the schematic section according to FIG. 5. Only major differences from the first embodiment will be described here, in particular, which means that the above remarks and explanations may still apply accordingly or in supplementary manner.

In FIG. 5, a transmission 21 is shown, particularly a gearwheel or gear or planetary transmission 21, of the inhaler 1 or of the conveying device 5 for advancing or further conveying the carrier. However, theoretically, any other suitable transmission may be used.

It has to be noted that only part of the carrier is shown in FIG. 5.

Particularly preferably, a free running or freewheeling clutch 22 is associated to the transmission, or with a drive wheel or gearwheel, particularly the central, main or sun wheel 14, or is arranged or integrated therein. In the embodiment shown, the free running 22 comprises a drive element 23 with at least one preferably tangentially and/or radially projecting finger 24 (most preferably five fingers 24). The drive element 23 engages in one direction of rotation (anticlockwise direction in the embodiment shown) in interlocking engagement by means of the finger 24 or fingers 24 on an associated driven element 25 connected with the wheel 14, in order to drive the latter in this direction. In particular, inner teeth 25*a* are formed on the associated driven element 25 on which the fingers 24 can engage. In the other direction or rotation the elastic fingers 24 can deflect and glide or slip through.

The wheel 14 preferably drives associated (planet) gears 27 of the transmission 21 via optional intermediate gears 26.

The gears 27 are preferably arranged coaxially and/or connected with the wheels 12 (not shown in FIG. 5) for guiding and/or conveying the carrier. Particularly preferably, each gears 27 is mounted about or with an associated wheel 12 on a common axle or axis, and/or these two are of integral construction. For example, the gears 27 may be formed on the wheels 12 or vice versa. In general, the gears 27 are associated to the driving wheels 12, wherein the gears 27 can be driven by any suitable transmission or drive means.

It has to be noted that the number and arrangement of wheels 12, deflectors 8 and/or any other even stationary guiding means for guiding the carrier/blister strip 3 can be chosen as appropriate and/or may vary depending on the length and/or dimension of the carrier and/or on the number of carriers. The same applies for the path of the carrier in the inhaler 1. It may be e.g. oval, or meander-like or even in different planes.

In the second embodiment, the inhaler 1 comprises preferably only two (driven) wheels 12 (not shown) engaging with the carrier/blister strip 3 for moving onward the carrier. In FIG. 5, only the two gears 27 associated to these wheels 12 are shown. These wheels 12 preferably form reflectors 8 in the sense of the first embodiment.

In addition to the wheels 12, the carrier is guided mainly by stationary walls 10, 11 and by the moveable guide element 13. The guide element 13 is moveable as already described, preferably by means of a protrusion 43 extending preferably transversaley from the guide element 13 and engaging into a control curve (not shown) formed on the inner side of the cover 15 to ensure the desired and in particular positive movement of the guide element 13 back and forth in response to the pivotal movement (opening and closing) of the cover 15.

The inhaler 1 or the conveying device 5 preferably has a non-return mechanism 28 to safely prevent undesirable reversing of the carrier and/or to form a defined end stop to the movement of the carrier. The non-return mechanism 28 preferably works on the conveying device 5 or its transmission 21 or gear, e.g. in the embodiment shown on one gear 27 or multiple gears 27 or on a suitable tooth arrangement formed e.g. by gears 27 or wheels 12. For example, the non-return mechanism 28 may be formed by an, in particular, elastically biased locking latch or the like as schematically shown in FIG. 5 which prevents the unwanted backwards rotation and reversing. Alternatively or additionally, the non-return mechanism 28 may also act on the carrier itself.

In the embodiment shown the drive element 23 is preferably coupled in a driving relationship with the cover 15, preferably with a predetermined torsional play, so that the drive element 23 is rotated at the same time during opening and closing, after the cover 15 has overcome the torsional play.

In one direction of rotation the free running 22 locks in place and rotates the wheel 14 in order to drive the wheels 27 to convey the carrier onwards by means of the wheels 12. In the other direction of rotation the free running 22 comes into effect or rotates or slips through, at least under the effect of the optional non-return mechanism 28, so that the carrier is no longer moved backwards or at most is moved backwards as far as the stop or the barrier of the non-return mechanism 28 allows. This reversing as far as a defined stop by means of the non-return mechanism 28 can be achieved by corresponding frictional or forceful engagement of the free running 22 in the reverse direction and/or it can be used for highly accurate positioning of the carrier.

Preferably, the inhaler 1 is constructed such that the carrier is initially always advanced somewhat too far as it moves on to the next receptacle. Before the receptacle is opened, the carrier is then moved back to the travel limiter (end stop) or until the non-return mechanism 28 comes into effect. Thus, the receptacle which is to be opened is initially positioned very precisely in the position in which opening takes place, particularly just before moving it up to the opening elements 16.

Particularly preferably, the reversing of the carrier or of the receptacle which is to be opened, up to a defined end stop (formed or defined by the non-return mechanism 28), is used in the alternative already described above (advancing of the carrier only when the cover 15 is shut) so that during the initial opening of the inhaler 1 or of the cover 15 the carrier is moved back to the stop and the receptacle which is to be opened is accurately positioned relative to the opening element 16. The actual opening of the receptacle then takes place in the course of the further opening movement of the cover 15, as already explained.

Generally speaking it should be pointed out that the free running 22 may also be constructed in some other way. The non-return mechanism 28 can also be formed in some other way. In particular the non-return mechanism 28 may if necessary also act directly on the carrier 2, optionally even directly on the receptacles or blister pockets 4.

The inhaler 1 or its housing 19 has in particular a flattened or indented (concave) side or edge. This flattened or indented side is particularly preferably formed by a portion 29 of the housing 19 of the inhaler 1 and/or by a portion 30 of the cover 15. The portion 29 serves in particular for holding or gripping the inhaler 1 or as an abutment surface for a finger, especially a thumb, of the user (not shown). The portion 30 serves in particular as an actuating surface, preferably for a finger or thumb of the user (not shown), during opening or for the purpose of opening the cover 15. When the inhaler 1 is closed, the two portions 29 and 30 are preferably located side by side and form, in particular, an at least substantially continuous outer surface of the inhaler 1. To open the cover 15 the two portions 29 and 30 can preferably be pushed apart. This allows very simple and/or intuitive operation.

The inhaler 1 comprises a life span blocking device (LSB) 31 further use or operation of the inhaler 1 in the blocking state, in particular when operation or use of the inhaler reaches or exceed a predetermined number of operations of uses. After operating or using the inhaler 1 for a predetermined number of operations or uses (e.g. number of receptacles or blister pockets 4), in the present embodiment e.g. after 30, 33, 47 or 60 applications, the LSB 31 enters into the blocking state and the inhaler 1 is locked up completely in order to avoid any further inadvertent applications.

The number of operation or uses can be detected or counted differently. Preferably, the opening and/or closing of cover 12 or the actuation of any other actuation element of the inhaler 1 may be detected and/or counted. In addition or alternatively, any onward movement of the carrier may be detected and/or counted.

Additionally or alternatively to these actions to determing when the blocking stage shall he entered, it may be detected when the last receptacle or blister pocket has been moved into the removal position or has been emptied and/or when the end of the carrier has been reached. Alternatively or additionally, it is possible to detect and count the inhalation, e.g. the occurance of an air stream 1, and/or the actual discharge of formulation 2 through mouthpiece 7. Therefore, the term "when operation or use of the inhaler 1 reaches or exceeds a predetermined number of operations or uses" has to understood in a very broad sense and that the number of operations or uses can be counted or detected directly or indirectly.

Figure 5:
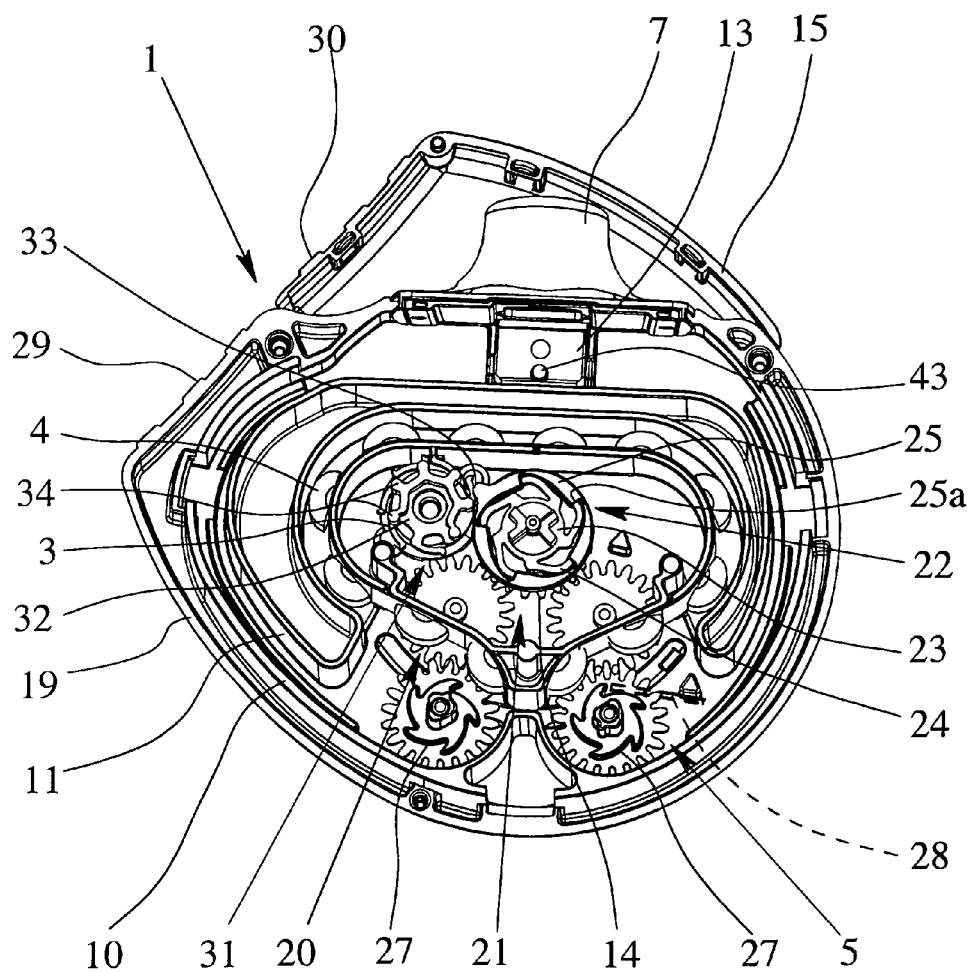
FIG. 5 is a schematic view of an inhaler according to a second embodiment in the closed state.

As shown in FIG. 5, the LSB 31 comprises preferably a control wheel 32. In particular the control wheel 32 is rotatable by the conveying device 5 or transmission 21, in particular by the central or main wheel 14 or drive member 25. In the shown embodiment, the control wheel 32 is rotated by at least or only one tooth 33 formed at drive member 25. The LSB 31 or the control wheel 32 is preferably driven by gear reduction, in particular that it rotates stepwise each x-th step of the stepwise actuation of the inhaler 1 or movement of the carrier (wherein x is preferably a natural number of 2 to 100). This kind of gear reduction is realized in the shown embodiment in that the tooth 33 is meshing with respective teeth 34 formed at the control wheel 32. If desired or necessary instead of one tooth 33 multiple teeth 34 could be used in particular in different planes. Further, teeth 34 in different planes and/or with different radial extension and/or different peripheral position could be used. Thus and in general, any desired gear reduction can be realized, in particular with stepwise movement of the driven wheel 32, preferably at or by predetermined incremental movement(s) of the driving wheel 25. However, other constructional solutions are possible as well.

It has to be noted that the control wheel 32 does not have to be necessarily a wheel or gear or the like. Instead, it may be any moveable, pivotable or rotatable control part. In the present embodiment, for example, the control wheel 32 is not rotated completely during the operation of the inhaler 1, but only up to a certain angle, i.e. about 180° to 270°, from its initial position to the final position when the blocking state is reached. Therefore, the control wheel 32 does not need a closed loop or crown of teeth 34, but only some teeth 34 as necessary in the present embodiment. Accordingly, the term "control wheel" has to be understood in a very broad sense in order to encompass all kinds of control parts.

Further, it has to be noted that the control wheel 32 can form part of a counting device of the inhaler 1 and/or could be driven by a counting device of the inhaler 1.

Figure 6:
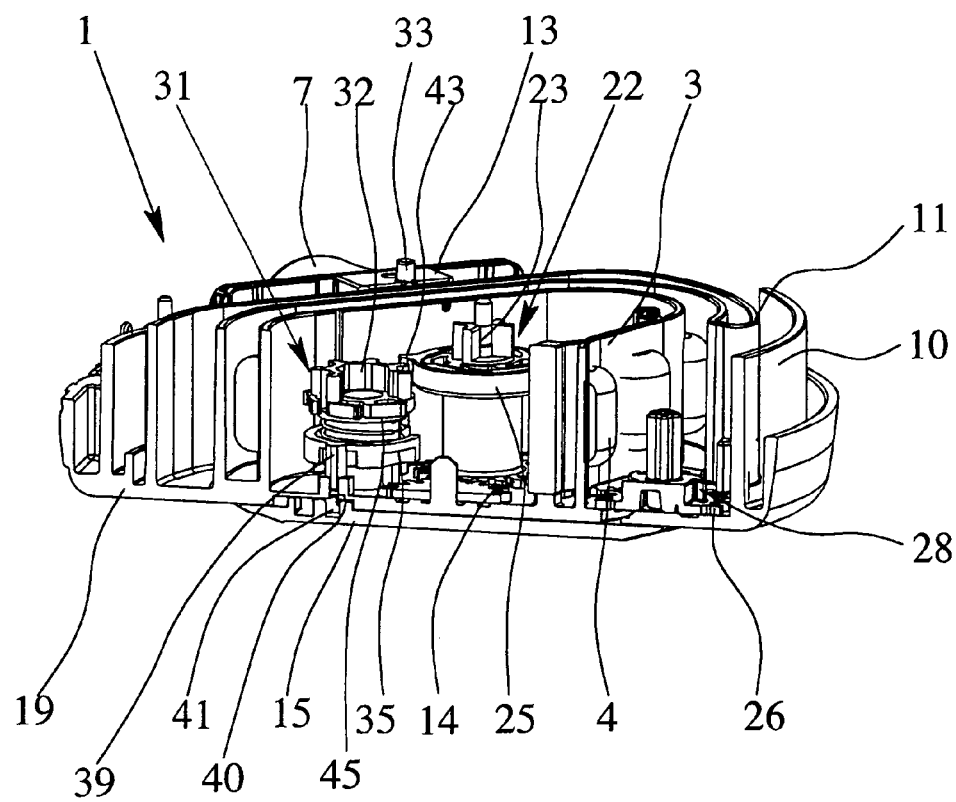
FIG. 6 is a schematic partial view of the inhaler with unblocked cover.
Figure 7:
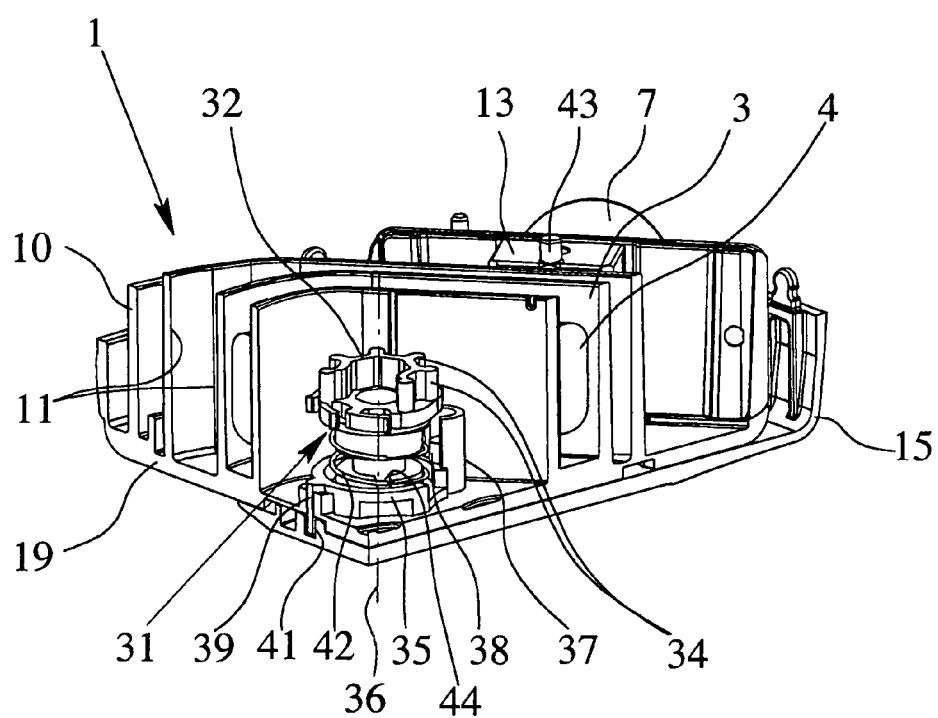
FIG. 7 is a schematic partial view of the inhaler with blocked cover.

FIGS. 6 and 7 show partial sectional views of the inhaler 1. In FIG. 6, the inhaler 1 or LSB 31 is not in the blocking state. In FIG. 7, the inhaler 1 or LSB 31 is in the blocking state.

In the present embodiment, the LSB 31 comprises preferably a control member 35 associated to the control wheel 32. The control member 35 is preferably arranged coaxially and/or adjacent to the control wheel 32, in particular on an axle of the control wheel 32 or vice versa. The control member 35 is preferably axially moveable along or parallel to the rotational axis 36 of the control wheel 32.

The control member is axially moveable relative to the control wheel 32. In the shown embodiment, the control wheel 32 is not axially moveable, but only the control member 35. However, a complementary construction is also possible.

The control member 35 is guided, preferably by a guidance 37 guiding a portion 38 of the control member 35 and/or by a locking element 39 and/or by any other suitable construction, such that the control member 35 is moveable preferably axially and/or in any other suitable, preferably in a straight direction and/or such that the control member 35 can not rotate. For example, the essentially cylindrical portion 38 formed at the side of the control member 35 is guided in a hollow structure formed by the guidance 37. In the present embodiment, the locking element 39 is preferably bolt like and/or longitudinal and/or guided in a throughhole 40 preferably formed in the housing 19 and/or by any other preferably stationery component of the inhaler 1.

In the present embodiment the locking element 39 is preferably interconnected and/or formed by the control member 35. However, other construction solutions are also possible.

Preferably, the locking element 39 is arranged transversely offset to the rotational axis 36 and/or extends or moves parallel to the rotational axis 36.

The LSB 31 is designed such that it can block movement or opening of the cover 15 in the blocking state. In particular, the locking element 39 can interlock in its interlocking position the cover 15 with the housing 19 or any other stationery component of the inhaler 1.

FIG. 6 shows the locking element 39 in its non-interlocking position. FIG. 7 shows the locking element 39 in its interlocking position. In the interlocking position, the locking element 39 engages into a corresponding recess 41 formed in the cover 15. However, the locking element 39 could also engage with any other stop or part or the like of the cover 15.

It has to be noted that the cover 15 can be locked in a form-fit manner in the blocking state in order to securely prohibit any further operation, in particular any opening of the cover 15.

Preferably the locking element 39 is biased into its interlocking position, in particular by spring force. In the present embodiment, the locking element 39 is biased by spring 42 into its interlocking position. In particular, the spring 42 acts on the control member 35, namely biases the control member 35 in an axial direction and, thus, the locking element 39 into the interlocking position.

In order to ensure that the locking element 39 is released from its non-interlocking position shown in FIG. 6 and/or forced to move into its interlocking position only when the blocking state is reached, the LSB 31 holds the locking element 39 in its non-interlocking position, until the blocking state is entered. In particular, the control wheel 32 and/or the control member 35 comprise respective keying means, e.g. at least one radial notch and/or at least one complementary recess, slit or groove 44, such that the control member 35 can move preferably axially from its initial position with non-interlocking locking element 39 shown in FIG. 6 into the shifted position with the locking element 39 in its interlocking position shown in FIG. 7 only in one rotational position (shown in FIG. 7) of the control wheel 32 relative to the control member 35, namely when the blocking state is entered or reached and/or when the keying means fits and/or the locking element 39 is released.

For example, two notches (e.g. non identical) may be formed at the inner periphery of an annular part of the control member 35. The notches may extend radially inwardly. Two complementary grooves 44 may be formed at an annular, flange-like part of the control wheel 32. However, this principle can be reversed. The annular part of the control member 35 fits over the annular part of the control wheel 32, but can move axially in the desired manner to move the locking element 39 into its interlocking position only in the predetermined rotational position named above when the blocking state is entered, i.e. when the control wheel 32 has been rotated sufficiently.

The spring 42 is preferably arranged and/or supported between the control wheel 32 and the control member 35. In particular, it surrounds an axle of the control wheel 32. This allows a very compact construction. However, other constructional solutions are possible.

In the present embodiment, the locking element 39 is biased into its interlocking position indirectly, namely in that the spring 42 acts on the control member 35. However, the spring 42 could also act directly on the locking element 39.

In the present embodiment, the control member 35 is interconnected with or forming the locking element 39. However, the control member 35 and the locking element 39 could also be formed by two separate parts.

It has to be noted that the LSB 31, in particular its control wheel 32, is preferably provided with a lock against reverse movement or rotation and/or against undesired movement or actuation, e.g. when the inhaler 1 drops. Further, the LSB 31 preferably comprises a ratchet mechanism in order to avoid any undefined movement of a component of the LSB 31 such as the control wheel 32 or locking element 39. In the present embodiment, this lock is formed by at least one snap arm 45, in particular multiple snap arms 45, in particular formed at the periphery of the control wheel 32. The at least one snap arm 45 may interact with another component, e.g. the housing 19 or any other stationery component, of the inhaler 1 so that a ratchet mechanism is formed and/or that the control wheel 32 can be rotated in only one direction. However, other constructional solutions are possible as well.

In the present embodiment, the conveying device 5 or its associated transmission 21 drives or actuates the LSB 31, in particular the control wheel 32 of the LSB 31. However, other constructional solutions are possible as well. In particular, the LSB 31 could also be driven by opening and/or closing of the cover 15 and/or by the onward movement of the carrier. Alternatively, the LSB 31 could be actuated by the carrier, i.e. when the carrier reaches a predefined position or the like. Such or a similar alternative will be described in the following with reference to a third embodiment of the inhaler 1.

Figure 8:
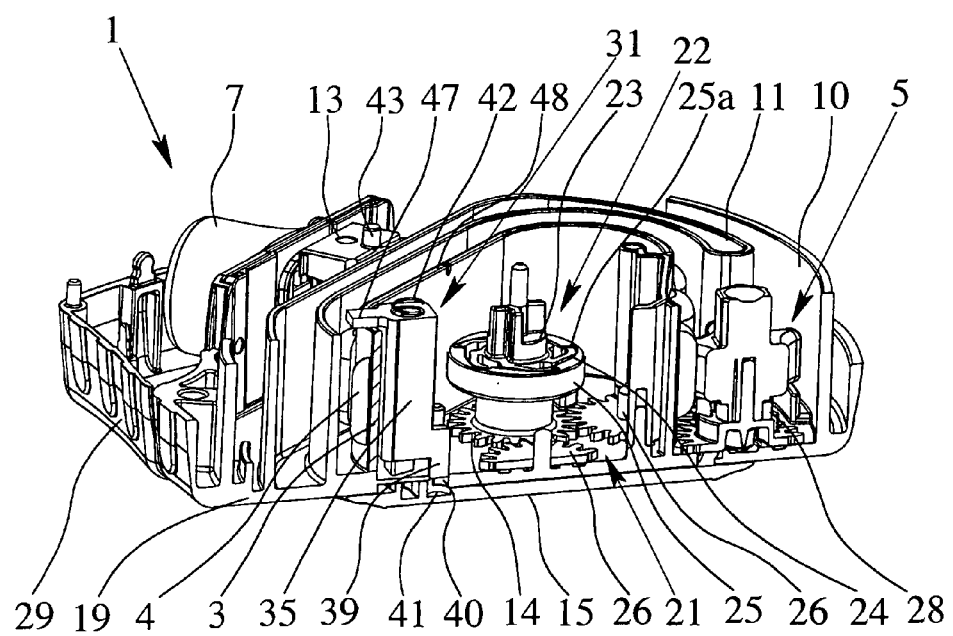
FIG. 8 is a schematic perspective view of part of a inhaler according to a third embodiment with unblocked cover.
Figure 9:
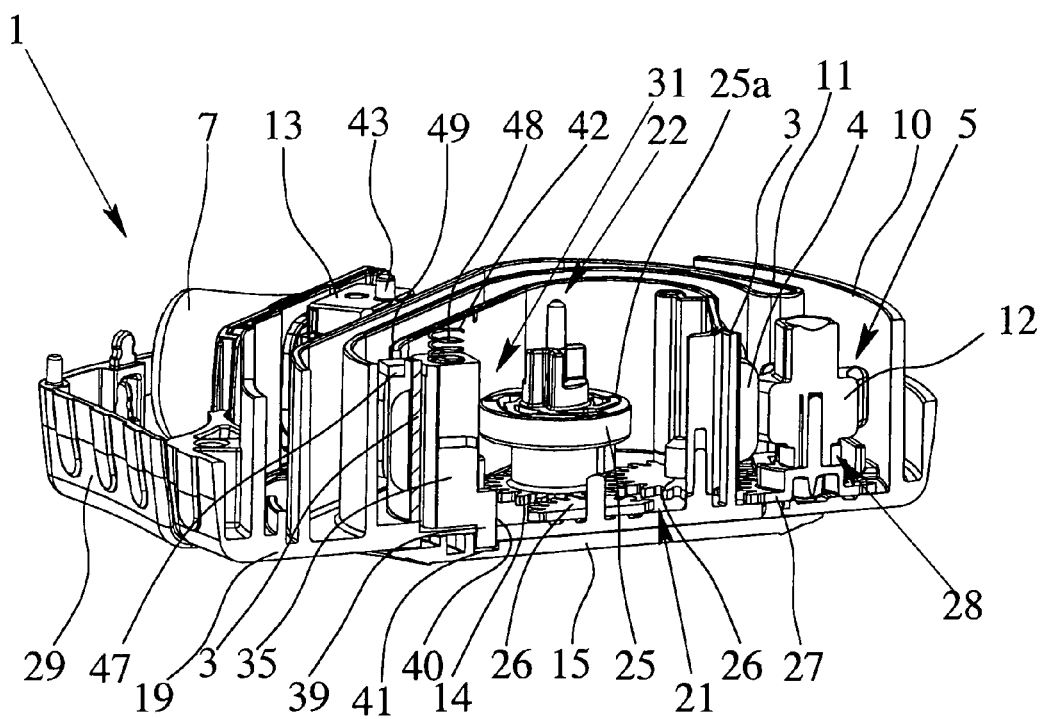
FIG. 9 is a schematic view of the part of the inhaler with blocked cover.

FIGS. 8 and 9 show schematically partial sectional views of the inhaler 1 according to a third embodiment. FIG. 8 shows the inhaler 1 with unblocked cover 15, i.e. in a non-blocking state. FIG. 9 shows the inhaler 1 with blocked cover 15, i.e. in the blocking state.

The third embodiment comprises a LSB 31 different than the second embodiment. Therefore, the following description will focus on these differences. However, the other aspects and features of the previous embodiments, in particular of the second embodiment, will apply correspondingly or additionally.

In the third embodiment, the carrier controls or actuated the LSB 31. In particular, the carrier controls or actuates the locking element 39.

The locking element 31 is guided such that it can move longitudinally. This is realized by a respective guidance of part of the locking element 39, in particular of the optional control portion or member 35 which may be held slidingly by a stationery component 46 of the housing 19 as schematically indicated in FIG. 8. However, other constructional solutions are possible as well.

The locking element 39 is biased into the interlocking position by spring 42 which may act directly on the locking element 39 or (as shown) on the optional control member 35.

In the third embodiment, the carrier holds the locking element 39 in its non-interlocking position and releases the locking element 39 into the interlocking position when the blocking state is entered and/or when the carrier moves into a predetermined release position shown in FIG. 9.

Preferably, the LSB 31, in particular the locking element 39, the control member 35 or a control part 47 extending from the locking element 39 or control member 35, interacts with the rim or edge 48 of the carrier such that the locking element 39 is held in its non-interlocking position during normal operation of the inhaler 1. Only when the blocking state is entered, in particular when the carrier reaches a certain predetermined position, the locking element 39 is released and/or moved into its interlocking position. This is preferably achieved by a recess 49 formed in the carrier, in particular at the edge 48 of the carrier, at a respective position such that the LSB 31 is actuated or released when the carrier reaches the predetermined position (end position) for activating or entering the blocking state.

When the carrier reaches the predetermined position, the control part 47 is not held any more by the edge 48, but can move into the recess 49 so that the control member 35 and/or locking element 39 can move from the non-interlocking position into the interlocking position, in particular due to the spring 42 biasing the control member 35 and/or locking element 39 into the interlocking position, as shown in FIG. 9.

Preferably, the locking element 39 and/or the control part 47 interacting with the carrier can move in a locking direction when the locking element 39 moves from its non-interlocking position into its interlocking position. This locking direction preferably extends at least essentially parallel to the main plane of the carrier, in particular a flat side of the carrier. Additionally or alternatively, the locking direction extends at least essentially transversely or perpendicular to the longitudinal extension of the carrier and/or to the direction of onward movement of the carrier.

This direction is preferred due to the relatively high rigidity of the blister strip 3 transversely to its longitudinal direction and parallel to its main plane. However, other construction solutions are possible as well. In particular, its possible that the control part 47 does not interact with the edge 48 and/or in the described preferred direction, but with any other part of the carrier and/or in any other direction. Accordingly, the recess 49 or any indention or the like may be located at any other appropriate portion of the carrier.

In the shown embodiments, the locking direction preferably extends parallel to the rotation axis of the wheels 12 and/or the pivotal axis of the cover 15.

Preferably, the inhaler 1 is constructed such that the cover 15 can be closed always, i.e. also in the blocking state. This can be achieved for example in that the locking element 39 can interlock the cover 15 only when the cover 15 has been closed. Alternatively or additionally, a respective ramp can be provided so that the locking element 39 can be released and move—e.g. only partly—into its protruding interlocking position even if the cover 15 has not been closed yet. When the cover 15 is closed, the locking element 39 can ride on the ramp and is lifted or moved backwards so that the locking element 39 can enter the recess 41 in the cover 15 when the cover 15 reaches its closed position. Then, the cover 15 will be interlocked in a form-fit manner as already described. However, other construction solutions are possible. For example, a sequence of ramps and/or shoulders can be formed at the cover 15 so that the cover 15 can be locked in steps during closing when the locking element 39 has been released, i.e. the blocking state has been entered.

In the present embodiment, the locking element 39 engages with or interlocks the cover 15. However, the locking element 39 can alternatively interlock or block any other component that has to be moved or is moveable for or during operation or use of the inhaler 1, e.g. any other actuation element, the conveying device 5, the wheel 14, the transmission 21, the carrier or the like.

Individual features and aspects of the embodiments and the embodiments itself may be combined with one another as desired and/or used in other inhalers 1 and/or independently. In particular the inhaler 1 of the first embodiment comprises a LSB 31 according to the second or third embodiment.

Some preferred ingredients and/or compositions of the preferably medicinal formulation 2 are listed below. As already mentioned, they are in particular powders or liquids in the broadest sense. Particularly preferably the formulation 2 contains the following:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2(5.6-diethyl-indan-2-ylamino)-1-hydroxy-ethyl]-8-hydroxy-1H-quinolin-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-aceticacid)-1,1-dimethyl-ethylamino]-ethyl}-4H-benzo[1,4]oxazin-3-one 8-{2-[1,1-dimethyl-2-(2.4.6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3.4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl] urea 4-(2-{6-[2-(2.6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

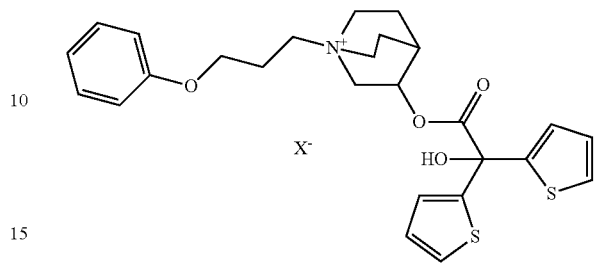

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

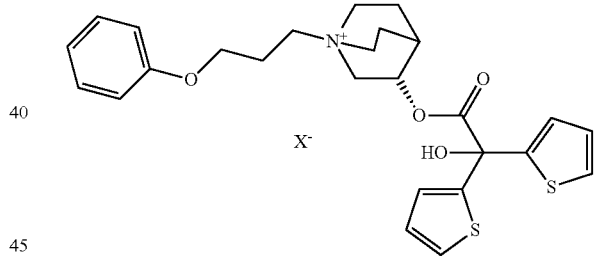

AC-1-en wherein $X^-$ may have the above-mentioned meanings. Other preferred anticholinergics are selected from the salts of formula AC-2

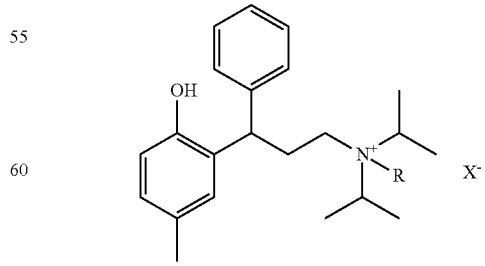

AC-2 wherein R denotes either methyl or ethyl and wherein $X^-$ may have the abovementioned meanings. In an alternativen embodiment the compound of formula AC-2 may also be present in the form of the free base AC-2-base.

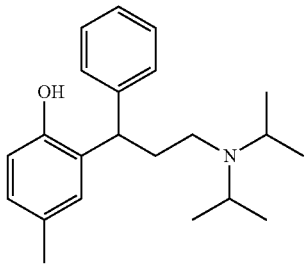

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
cyanomethy16α,9α-difluoro-11β-hydroxy-16α-methyl-3-oxo-17α-(2,2,3,3-tertamethylcyclopropylcarbonyl)oxy-androsta-1,4-diene-17β-carboxylate
optionally in the form of the racemates, enantiomers or diastereomers thereof and optionally in the form of the salts and derivatives thereof, the solvates and/or hydrates thereof Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3.4-c]-1,2,4-triazolo[4.3-a]pyridine
9-cyclopentyl-5,6-dihydro-7-ethyl-3-(tert-butyl)-9H-pyrazolo[3.4-c]-1,2,4-triazolo[4.3-a]pyridine
optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane-acetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-[4-(N,N-diethylamino)-1-oxo-2-buten-1-yl]amino -7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]-amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenylamino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl]amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino }-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino }-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinylcarbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylaminoethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof According to the invention the acid addition salts of the betamimetics are preferably selected from among the hydrochloride, hydrobromide, hydriodide, hydrosulphate, hydrophosphate, hydromethanesulphonate, hydrocitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules, as disclosed in EP 1 003 478 A1 or CA 2297174 A1.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

LIST OF REFERENCE SIGNS 1 inhaler
2 formulation
3 blister strip
4 lister pocket
5 conveying device
6 removal device
7 mouthpiece
8 deflector
9 annular segment
10 outer wall
11 inner wall
12 wheel
13 guide element
14 wheel
15 cover
16 opening element
17 groove
18 control curve
19 housing
20 radial stop
21 transmission
22 free running
23 drive element
24 finger
25 driven element
25a inner teeth
26 intermediate gear
27 gear
28 non-return device
29 housing portion
30 cover portion
31 life span blocking devie
32 control wheel
33 tooth
34 teeth
35 control member
36 rotational axis
37 guidance
38 portion
39 locking element
40 throughhole
41 recess (cover)
42 spring
43 protrusion
44 groove
45 snap arm
46 component
47 control part
48 edge
49 recess (carrier)
L air stream
P arrow The invention clamed is:

1. An inhaler (1) for discharging a powdered formulation (2) in multiple doses one after the other,
with an outlet or mouthpiece (7) for discharging a nebulized or atomized formulation (2),
with a cover (15) moveable between a closed position covering the outlet or mouthpiece (7), and an open position uncovering the outlet or mouthpiece (7),
with a life span blocking device (31) for blocking further use or operation of the inhaler (1) in a blocking state, when operation or use of the inhaler (1) reaches or exceeds a predetermined number of operations or uses,
wherein the life span blocking device (31) blocks movement or opening of the cover (15) in the blocking state, and
wherein the life span blocking device (31) comprises a control member (35) and a control wheel (32) rotatable relative to the control member (35), wherein the control wheel (32) and/or the control member (35) comprise keying means so that axial movement of the control member (35) relative to the control wheel (32) is possible only in one rotational position of the control wheel (32) relative to the control member (35) to release a locking element (39).

2. The inhaler according to claim 1, characterized in that the inhaler (1) is constructed such that the cover (15) can be closed in the blocking state.

3. The inhaler according to claim 1, characterized in that the life span blocking device (31) comprises a locking element (39) interlocking in the interlocking position the cover (15) with a housing (19) or another stationary component of the inhaler (1).

4. The inhaler according to claim 3, characterized in that the locking element (39) is biased into the interlocking position by spring force.

5. The inhaler according to claim 3, characterized in that the locking element (39) is held in a non-interlocking position and released or forced into the interlocking position in the blocking state.

6. An inhaler (1) for delivering a powdered formulation (2) in multiple doses one after the other,
with a life span blocking device (31) for blocking further use or operation of the inhaler (1) in a blocking state, when operation or use of the inhaler (1) reaches or exceeds a predetermined number of operations or uses,
wherein the life span blocking device (31) comprises a locking element (39) which is biased into an interlocking position for blocking further use or operation of the inhaler (1),
wherein the locking element (39) is held in a non-interlocking position and released or forced into the interlocking position in the blocking state, and
wherein the life span blocking device (31) comprises a control member (35) and a control wheel (32) rotatable relative to the control member (35), wherein the control wheel (32) and/or the control member (35) comprise keying means so that axial movement of the control member (35) relative to the control wheel (32) is possible only in one rotational position of the control wheel (32) relative to the control member (35) to release the locking element (39).

7. The inhaler according to claim 6, characterized in that the control member (35) is interconnected with or forming the locking element (39), and/or that the control member (35) is biased axially by means of a spring (42), acting between the control wheel (32) and the control member (35), wherein the spring (42) biases the locking element (39) into or in the interlocking position.

8. The inhaler according to claim 6, characterized in that the control wheel (32) is actuated by gear reduction stepwise by an element (25).

9. The inhaler according to claim 1, characterized in that the inhaler (1) comprises a blister strip (3), with a plurality of blister pockets (4), containing the formulation (2) in doses.

10. The inhaler according to claim 9, characterized in that the inhaler (1) comprises a conveying device (5) for moving stepwise onward the blister strip.

11. The inhaler according to claim 10, characterized in that the conveying device (5) or an associated transmission (21) drives the life span blocking device (31).

12. The inhaler according to claim 10, characterized in that the conveying device (5) or an associated transmission (21) is driven by opening and/or closing of the cover (15).

13. The inhaler according to claim 6, characterized in that the inhaler (1) comprises a blister strip (3) with a plurality of blister pockets (4) containing the formulation (2) in doses and a conveying device (5) for moving stepwise onward the blister strip (3), wherein the conveying device (5) or an associated transmission (21) drives the control wheel (32).

* * * * *